United States Patent [19]

Kovacs et al.

[11] Patent Number: 5,068,253

[45] Date of Patent: Nov. 26, 1991

[54] TREATMENT OF A MICROBIAL INFECTION WITH DRUGS CONTAINING PARA-ACETAMIDOBENZOIC ACID

[75] Inventors: Joseph Kovacs, Potomac; Henry Masur, Bethesda; Carmen Allegra, Gaithersburg, all of Md.

[73] Assignee: The United States of America as represented by the Department of Health and Human Services, Washington, D.C.

[21] Appl. No.: 551,521

[22] Filed: Jul. 11, 1990

[51] Int. Cl.$^5$ ............................................. A61K 31/185
[52] U.S. Cl. ....................................................... 514/553
[58] Field of Search ........................................ 514/553

[56] References Cited

U.S. PATENT DOCUMENTS

| 4,814,323 | 3/1989 | Andrieu et al. | 514/11 |
| 4,835,177 | 5/1989 | Durette | 514/19 |
| 4,866,035 | 9/1989 | Durette | 514/19 |
| 4,866,036 | 9/1989 | Durette | 514/19 |
| 4,868,155 | 9/1989 | Durette et al. | 514/19 |
| 4,868,157 | 9/1989 | Durette | 514/19 |

OTHER PUBLICATIONS

Pedersen et al., "The Efficacy of Inosine Pranobex in Preventing the Acquired Immunodeficiency Syndrome in Patients with Human Immunodeficiency Virus Infection", The New England Journal of Medicine, vol. 322, Jun. 21, 1990, vol. 322, No. 25, pp. 1757–1809.

Primary Examiner—Stanley J. Friedman
Attorney, Agent, or Firm—Cushman, Darby & Cushman

[57] ABSTRACT

The present invention relates to a method of treating or preventing a microbial infection, such as *Pneumocystis carinii* or *Toxoplasma gondii*, in a patient comprising administering to the patient an antimicrobially effective amount of p-acetamidobenzoic acid or a pharmaceutically acceptable salt thereof so that the microbial infection is inhibited. P-acetamidobenzoic acid or an acceptable salt thereof can be used to treat infections caused by *Pneumocystis carinii, Toxoplasma gondii*, Plasmodium species and other microorganisms containing the enzyme dihydropteroate synthetase such as most bacteria and some yeasts. The method of the present invention is particularly applicable in situations where the patient is immunosuppressed.

8 Claims, No Drawings

TREATMENT OF A MICROBIAL INFECTION WITH DRUGS CONTAINING PARA-ACETAMIDOBENZOIC ACID

BACKGROUND OF THE INVENTION

1. Field of the Invention

The present invention relates to a method of preventing or treating a microbial infection, in particular, an infection by *Pneumocystis carinii* or *Toxoplasma gondii*.

2. Background Information

*Pneumocystis carinii* and *Toxoplasma gondii* are pathogens of immunosuppressed hosts which have become more important clinically with the Acquired Immunodeficiency Syndrome (AIDS) epidemic. These pathogens cause serious infections in immunosuppressed patients including patients with cancer, organ transplants and AIDS. Currently, available agents for treatment and prevention of these infections in immunosuppressed patients are poorly tolerated by many patients, especially those with AIDS. Furthermore, administration of available agents is often via difficult routes such as intravenously or by aerosol.

Studies in rodents and humans have resulted in the implication that *P. carinii* possess a pathway for de novo folate synthesis that is susceptible to sulfonamides, and the enzyme dihydrofolate reductase (DHFR), which is susceptible to trimethoprim. More recent studies have documented the presence of these pathways in *P. carinii* and *T. gondii*. Since mammalian cells can not synthesize folates de novo, these metabolic pathways are an ideal target for the development of more effective anti-pneumocystis and anti-toxoplasma agents since the host would not be affected by the targeted action of such therapeutic agents.

The present inventors have discovered an agent having antimicrobial activity, (particularly anti-pneumocystis activity), suitable for use in patients, especially immunosuppressed patients.

SUMMARY OF THE INVENTION

It is an object of the present invention to provide an antimicrobial agent and a method of preventing or treating a microbial infection.

It is a further object of the present invention to provide an antimicrobial agent which is easily administered and well tolerated.

In one embodiment, the present invention relates to a method of treating or preventing a microbial infection in a patient comprising administering to the patient an antimicrobially effective amount of p-acetamidobenzoic acid or a pharmaceutically acceptable salt thereof so that the microbial infection is inhibited.

Various other objects and advantages of the present invention will become apparent to one skilled in the art from the following description of the invention.

DETAILED DESCRIPTION OF THE INVENTION

The present invention relates to a method of treating a microbial infection, for example, a pneumocystis infection or a toxoplasma infection. The method is particularly applicable in situations where the patient is immunosuppressed, such as by cancer or AIDS. The antimicrobial agent used in the present method is p-acetamidobenzoic acid (PAcBA) or a soluble salt thereof, such as, for example, the PAcBA salt of 1-dimethylamino-2-propanol. (The term microbial as used herein includes bacteria, fungi, yeast and protozoans)

In the present method, inosine can be used in complexation with the PAcBA salt of dimethylamino-2-propanol (such a complex being known as isoprinosine).

Furthermore, in the present method, an inhibitor of the enzyme dihydrofolate reductase (DHFR) can be used in combination with the antimicrobial agent. Possible inhibitors for use in the present invention include, but are not limited to, trimethoprim, pyrimethamine and trimetrexate.

Without being limited to a particular mode of activity, PAcBA appears to exert its antimicrobial effect by inhibiting the enzyme dihydropteroate synthase (DHPS). Accordingly, it is contemplated that PAcBA can be effective against any organism that utilizes DHPS and is susceptible to DHPS inhibitors, such as Plasmodium species (which cause malaria), in addition to those organisms named above.

In the method of the present invention, a composition comprising an antimicrobially effective amount of PAcBA in a pharmaceutically acceptable carrier is administered to a patient, for example, an immunosuppressed patient, orally or parenterally (intravenously or intramuscularly). Preferably, a salt of the active agent, PAcBA is present in the composition. The patient is treated with an effective amount of the composition to prevent or inhibit microbial activity. The effective amount will vary depending on several factors such as, for example, the severity of the infection, the causative organism and the type of infection being treated. One skilled in the art can easily determine the effective amount of the composition for a particular patient given the patient's history and symptoms.

The following non-limiting examples are provided to aid in the understanding of the present invention. It is understood that modifications can be made in the procedure set forth, without departing from the true spirit of the invention.

EXAMPLE

The following assay, used previously to assess drug activity against *P. carinii* or *T. gondii* [Kovacs et al., J. Infectious Diseases 160:312–320 (1989)], was used to test drugs for their ability to adversely affect the metabolism of pneumocystis and toxoplasma.

Organisms

An animal model of *Pneumocystis carinii* pneumonia was used to obtain organisms. This model involves treating rats, usually Sprague-Dawley rats, with a corticosteroid, in the present case dexamethasone (1–2 mg/L of drinking water) for 6–10 weeks. Tetracycline is included in the water (1 mg/mL) to prevent bacterial superinfection. Such immunosuppressed rats will develop *P. carinii* pneumonia spontaneously, and *P. carinii* organisms are obtained by removing the lungs in a sterile manner, cutting up the lungs and disrupting them with a Stomacher (Tekmar), which makes a suspension of organisms and cells. The *P. carinii* organisms are then partially purified by Ficoll-Hypaque density gradient centrifugation, washed in phosphate buffered saline (PBS), and used in the following experiment.

The RH strain of *Toxoplasma gondii* were used in all experiments. Organisms are passed by intraperitoneal inoculation into Balb/c mice every 3 to 4 days. Organisms were harvested by lavaging the peritoneum of infected animals 3 to 4 days after inoculation. Organisms were resuspended in PBS, cells are removed by differential centrifugation, and organisms were then pelleted and utilized in the studies.

Drug Inhibition Assay

For drug inhibition studies, organisms are incubated with drugs at varying concentrations for 2-h in paraaminobenzoic acid-free (PABA-free) and folate-free RPMI before pulsing with [$^3$H]PABA.

Organisms are harvested after an 18-24 h pulse and washed twice in phosphate buffered saline (PBS). Folates are extracted as previously described [Allegra et al., J. Biol. Chem. 261:6478-6485 (1986)]. The organism pellet is heated at 100° C. for 1 min in 2% sodium ascorbate, pH 6.0, and 2% 2-mercaptoethanol; after centrifugation, the supernatant is treated with partially purified porcine kidney conjugase for 30 min at 37° C. to convert all folates to monoglutamates. After an additional boiling with sodium ascorbate and 2-mercaptoethanol, the folates are extracted into methanol using a C-18 cartridge (Sep-Pak, Waters Chromatography Division, Milford, Mass.) and concentrated under a stream of nitrogen.

The individual folates are resolved by high-performance liquid chromatography (HPLC) using a C8 μBondapak column (Waters Chromatography) under isocratic conditions; the running buffer is 15% ethanol and 85% Pic A (Waters Chromatography), pH 5.5 Radioactivity is determined by an in-line scintillation counter (Flow 1 Beta, model CR, Radiomatic Instruments, Tampa, Fla.). Unlabeled folates are included in each run as internal controls.

Results are presented as the percentage of total radiolabel incorporated into reduced folates compared with untreated controls.

Drugs

Drugs were obtained from the following sources: Isoprinosine (Newport Pharmaceutical); P-acetamidobenzoic acid (PAcBA), (Sigma Chemical Co.); inosine (Aldrich Chemical Co.); and 1-dimethylamino-2-propanol (Aldrich Chemical Co.). Isoprinosine is composed of inosine and the salt of PAcBA and 1-dimethylamino-2-propanol in a 1:3 molar ratio.

The results of the assay carried out on P. carinii are shown below in Table I.

TABLE I

| Drug | Concentration (M) | Results: % of Control | | | | | Mean |
|---|---|---|---|---|---|---|---|
| Isoprinosine | $1 \times 10 - 2$ | | | | | | |
| | $1 \times 10 - 3$ | | | | | | |
| | $1 \times 10 - 4$ | 2.1 | 2.8 | | | | 2 |
| | $1 \times 10 - 5$ | 25.2 | 10.3 | | | | 18 |
| | $1 \times 10 - 6$ | 73.7 | 62.7 | | | | 68 |
| | | 100 | 100 | | | | 100 |
| PAcBA | $1 \times 10 - 2$ | | | 2.6 | 11.2 | 2.4 | 5 |
| | $3 \times 10 - 3$ | | | 5.9 | 20.7 | 11.6 | 13 |
| | $1 \times 10 - 3$ | 16.8 | 24.7 | 14.1 | 23.3 | 19.6 | 20 |
| | $1 \times 10 - 4$ | 72.2 | 71 | 63.5 | 52.7 | 73.1 | 67 |
| | $1 \times 10 - 5$ | 100 | 84.8 | | 48.9 | | 78 |
| | $1 \times 10 - 6$ | 100 | | | 100 | | 100 |
| PAcBA as 1-dimethylamino-2-propanol salt | $1 \times 10 - 2$ | 0.4 | 0 | 0 | 0 | | 0 |
| | $1 \times 10 - 3$ | 1.4 | 0 | 1 | 0 | | 1 |
| | $1 \times 10 - 4$ | 7.9 | 19 | 15 | 20 | | 15 |
| | $1 \times 10 - 5$ | 40.5 | 82 | 44 | 43 | | 52 |
| | $1 \times 10 - 6$ | | 100 | 67 | 74 | | 80 |
| Inosine | $1 \times 10 - 2$ | 61.9 | 57.5 | 57.6 | | | 59 |
| | $1 \times 10 - 3$ | 100 | 100 | 100 | | | 100 |
| | $1 \times 10 - 4$ | | 69.8 | | | | 70 |
| 1-dimethylamino-2-propanol | $1 \times 10 - 2$ | 100 | 1.9 | 3.4 | 1.8 | | 27 |
| | $1 \times 10 - 3$ | 67 | 61 | 100 | 22.4 | | 63 |
| | $1 \times 10 - 4$ | 100 | 67.6 | | 71.3 | | 80 |
| | $1 \times 10 - 5$ | 95 | | | 65.4 | | 80 |

The first column indicates the drug tested. The concentration of the drug is indicated in the next column. The remaining columns represent the results of various test runs. The results are expressed as the percent activity compared to control. Thus, 100% is no inhibition (that is, the drug is ineffective) and 0% means total inhibition (that is, the drug is very effective).

As is seen in Table I, PAcBA produced considerable inhibition of P. carinii at concentrations of $1 \times 10^{-2}$ molar (M), $3 \times 10^{-3}$M, $1 \times 10^{-3}$M, and some inhibition at $1 \times 10^{-4}$M. When tested as a salt which is more soluble than the free acid, PAcBA was approximately 10-fold more potent. Isoprinosine has inhibition as well but most of it appears to be due to PAcBA or to the toxic effect of propanol.

Dihydropteroate synthase (DHPS) is an enzyme of the de novo folate synthesis pathway which is known to be susceptible to sulfonamides. PABBA has a structural similarity to PABA (paraamino benzoic acid), one of the substrates of DHPS. To determine whether DHPS is the target for PAcBA, a catalytic DHPS assay as previously described [Allegra et al., J. Clin. Invest. 85:371-379 (1990)] was used.

Briefly, assay tubes contain 5 mM $MgCl_2$, 5 mM DTT, 10 μM $H_2PtCH_2OPP$, 1 μM [$^3$H]pABA (final sp act, 2 Ci/mmol), and 40 mM Tris/HCl, pH 8.3, in a total reaction volume of 100 μl. Various concentrations of inhibitors are added as needed. Enzyme preparations were made by resuspending *P. carinii* or *T. gondii* organisms in 1 ml PBS, sonicating to disrupt the organisms, and pelleting the cellular debris. The supernatant was saved and used as the crude enzyme preparation. Reactions are initiated by the addition of 50 μl of enzyme preparation. After a 30-min incubation at 37° C. the reaction tubes are placed on ice to terminate the reactions, and then spotted onto 3×30-cm strips of 3 MM chromatography paper (Whatman Laboratory Products Inc.). The strips are developed in a descending chromatography tank using an elution buffer of 0.1M $KH_2PO_4$, pH 7.0. The origins containing the labeled products of the reaction are cut from the strips, placed in scintillation vials, and counted in a liquid scintillation counter (Packard Tri-Carb; Packard Instrument Co. Inc., Downers Grove, Ill.) 24 h after the addition of 9.5 ml of counting cocktail (3A70b; Research Products International Corp., Mt. Prospect, Ill.).

The results of the DHPS inhibition assay carried out on *P. carinii* (PC) and *T. gondii* (Toxo) using the indicated composition are shown below in Table II.

munosuppressed patients, is inhibited by PAcBA. The results suggest that PAcBA, alone or in combination with 1-dimethylamino-2-propanol or 1-dimethylamino-2-propanol and inosine (which is isoprinosine) provide an antimicrobial activity against organisms utilizing the de novo folate synthesis pathway, which includes the enzyme DHPS. Such organisms include, for example, *Plasmodium* species.

All publications mentioned hereinabove are hereby incorporated by reference.

While the foregoing invention has been described in some detail for purposes of clarity and understanding, it will be appreciated by one skilled in the art from a reading of this disclosure that various changes in form and detail can be made without departing from the true scope of the invention.

What is claimed is:

1. A method of treating or prventing a microbial infection in a patient comprising administering to said patient an antimicrobially effective amount of p-acetamidobenzoic acid or a pharmaceutically acceptable salt thereof so that said microbial infection is inhibited or prevented.

2. The method according to claim 1 wherein said microorganism utilize dihydropteroate synthase.

3. The method according to claim 2 wherein said microorganisms are pneumocystis or toxoplasma.

4. The method according to claim 1 wherein said patient is immunosuppressed.

TABLE II

| | Concentration (M) | | | | | Percent DHPS Inhibition | |
|---|---|---|---|---|---|---|---|
| *P. carinii* | | | | | | | |
| | | | | | | | Mean |
| PAcBA | $1 \times 10 - 3$ | 14.3 | 16.6 | 23.1 | 22.2 | | 19.1 |
| | $1 \times 10 - 4$ | 37.9 | 52.6 | 68 | 62.1 | | 55.2 |
| | $1 \times 10 - 5$ | 70.2 | 100 | | 92.2 | | 87.5 |
| 1-dimethylamino- | $1 \times 10 - 3$ | 81.7 | | | | | |
| 2-propanol | $1 \times 10 - 4$ | 91.6 | | | | | |
| | $1 \times 10 - 5$ | 100 | | | | | |
| Inosine | $1 \times 10 - 3$ | 100 | | | | | |
| | $1 \times 10 - 4$ | 100 | | | | | |
| | $1 \times 10 - 5$ | 100 | | | | | |
| Isoprinosine | $1 \times 10 - 3$ | 35.6 | | | | | |
| | $1 \times 10 - 4$ | 87.4 | | | | | |
| | $1 \times 10 - 5$ | 100 | | | | | |
| *T. gondii* | | | | | | | |
| | | | | | | | Mean |
| PAcBA | $1 \times 10 - 3$ | 8.1 | 8.5 | 5.1 | 7 | | 7.2 |
| | $1 \times 10 - 4$ | 51 | 35 | 21.4 | 23.4 | | 32.7 |
| | $1 \times 10 - 5$ | 80.4 | 80.5 | 68.4 | 80 | | 77.3 |
| | $1 \times 10 - 6$ | | | 83.4 | 100 | | 91.7 |
| | | | | | | Mean | |
| 1-dimethylamino- | $1 \times 10 - 3$ | 100 | | 100 | | 100.0 | |
| 2-propanol | $.1 \times 10 - 4$ | 93.6 | | 100 | | 96.8 | |
| | $1 \times 10 - 5$ | 100 | | 100 | | 100.0 | |
| Isoprinosine | | | | | | | Mean |
| | $1 \times 10 - 3$ | 8.9 | | 3.2 | 7.8 | | 6.6 |
| | $1 \times 10 - 4$ | 36.4 | | 19.5 | 28.3 | | 28.1 |
| | $1 \times 10 - 5$ | 63.5 | | 61.8 | 76.5 | | 67.3 |
| | $1 \times 10 - 6$ | | | | 100 | | 100.0 |

The results show inhibition of DHPS in *P. carinii* and *T. gondii* by PAcBA which suggests that DHPS is in fact the target of PAcBA's antipneumocystis activity. The results also show that DHPS activity in *Toxoplasma gondii*, another organism which infects im- 5. The method according to claim 4 wherein said patent has cancer or AIDS.

6. The method according to claim 1 wherein said salt is a p-acetamidobenzoate salt of dimethylamino-2-propanol.

7. A method of treating or preventing a microbial infection in a patient comprising administering to said patient an effective amount of a pharmaceuthical composition consisting essentially of p-acetainedobenzoic acid or a pharmaceutically acceptable salt there.

8. The method according to claim 1 wherein said microorganism is a bacteria, fungus or protozoan.

* * * * *